United States Patent
Krieg et al.

(10) Patent No.: US 7,482,592 B2
(45) Date of Patent: Jan. 27, 2009

(54) METHOD FOR COMBINING PET WITH MR PERFUSION AND DIFFUSION

(75) Inventors: Robert Krieg, Nürnberg (DE); Rainer Kuth, Herzogenaurach (DE); Ralf Ladebeck, Erlangen (DE); Ralph Oppelt, Uttenreuth (DE); Sebastian Schmidt, Erlangen (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 60 days.

(21) Appl. No.: 11/438,208

(22) Filed: May 23, 2006

(65) Prior Publication Data

US 2006/0284096 A1  Dec. 21, 2006

(30) Foreign Application Priority Data

May 24, 2005  (DE) ........................ 10 2005 023 906

(51) Int. Cl.
*G01T 1/166* (2006.01)
(52) U.S. Cl. ................................. 250/363.04; 600/411
(58) Field of Classification Search ............ 250/363.03, 250/363.04; 600/411; 324/309
See application file for complete search history.

(56) References Cited

U.S. PATENT DOCUMENTS

| | | | | |
|---|---|---|---|---|
| 4,939,464 A | * | 7/1990 | Hammer | 324/318 |
| 6,946,841 B2 | * | 9/2005 | Rubashov | 324/318 |
| 7,218,112 B2 | * | 5/2007 | Ladebeck et al. | 324/318 |
| 2003/0090267 A1 | * | 5/2003 | Rubashov | 324/318 |
| 2004/0044282 A1 | | 3/2004 | Mixon et al. | |
| 2004/0159791 A1 | * | 8/2004 | Hefetz | 250/363.03 |
| 2006/0052685 A1 | * | 3/2006 | Cho et al. | 600/407 |
| 2007/0075249 A1 | * | 4/2007 | Wang et al. | 250/363.04 |
| 2007/0102641 A1 | * | 5/2007 | Schmand et al. | 250/363.03 |

\* cited by examiner

*Primary Examiner*—David P Porta
*Assistant Examiner*—Mark R Gaworecki
(74) *Attorney, Agent, or Firm*—Harness, Dickey & Pierce, P.L.C.

(57) ABSTRACT

A method for determining positron emission measurement information in the context of positron emission tomography is disclosed. The method includes using a marker substance to carry out a positron emission measurement, in a body area of a subject to be examined, to determine positron emission measurement information, and at the same time, generating images of the body area to be examined by way of a second medical method with a time resolution suitable for determining perfusion and/or diffusion information. The method further includes using the images from the second method to determine perfusion and/or diffusion information for at least a part of the measurement period, and evaluating the positron emission measurement information as a function of the perfusion and/or diffusion information.

14 Claims, 2 Drawing Sheets

METHOD FOR COMBINING PET WITH MR PERFUSION AND DIFFUSION

The present application hereby claims priority under 35 U.S.C. §119 on German patent application number DE 10 2005 023 906.4 filed May 24, 2005, the entire contents of which is hereby incorporated herein by reference.

FIELD

The invention generally relates to a method for determining positron emission measurement information in the context of positron emission tomography.

BACKGROUND

In positron emission tomography, the distribution of a radioactive marker substance in the body of a subject being examined is determined, in order in this way to obtain functional images of the biochemical and physiological processes that are taking place. The time resolution that can be achieved in positron emission tomography is rather low compared to other diagnostic methods. The marker substance, also referred to as a radiotracer, requires very different times for reaching different regions of the body, these different times being due to the flow characteristics of the vascular system and to the diffusion properties at the blood-tissue interfaces. In a subsequent analysis of an image from positron emission tomography, it therefore remains unclear which concentration of the marker substance was available at which point in time and at which location.

Therefore, the informativeness of an examination carried out by positron emission tomography is greatly limited. It is possible only with difficulty to differentiate between disturbances which occur in the body of the subject being examined and which result in reduced metabolic activity, and disturbances which are themselves caused by reduced transport of substances into the tissue, for example deficient perfusion. On the other hand, a differentiation of this kind is of significance for a number of applications, for example in order to answer the question of what the prospects of success are for a revascularization procedure in a patient.

SUMMARY

An object of at least one embodiment of the invention is to provide an improved method for determining positron emission measurement information.

An object may be achieved by a method which comprises the following:
  using a marker substance to carry out a positron emission measurement, in a body area of a subject being examined, in order to determine positron emission measurement information,
  at the same time generating images of the body area to be examined by way of a second medical method with a time resolution suitable for determining perfusion and/or diffusion information,
  using the images from the second method to determine perfusion and/or diffusion information for at least a part of the measurement period, and
  evaluating the positron emission measurement information as a function of the perfusion and/or diffusion information.

The tracer substances, which are tagged with radionuclides, are therefore first introduced into the body in order to take part in the metabolism therein and to be detected by way of gamma detectors. Thus, over a defined measurement time, a positron emission measurement is carried out by which positron emission measurement information is obtained. The time resolution of this positron emission measurement information is rather low, with a typical value lying in the seconds range.

According to at least one embodiment of the invention, a further noninvasive medical imaging method is implemented at the same time in order to also generate images of the body area to be examined, for example the brain of a patient. Other body areas too can be recorded in the context of the positron emission measurement and the imaging by way of the second medical method, for example the upper body, in particular the heart or lungs. The second medical imaging method is chosen such that it has a better time resolution compared to the positron emission tomography, for example in the milliseconds range. The time constants defined by perfusion and diffusion processes in the tissue of a subject being examined represent the criterion for the required time resolution. Reference is made here, by way of example, to a typical diffusion constant in biological tissue lying at approximately $10^{-5}$ to $10^{-6}$ cm$^2$/s. Typical flow velocities, for example of blood or cerebrospinal fluid, lie at several cm/s.

The time resolution of the images from the second medical method is sufficient, according to at least one embodiment of the invention, to determine perfusion and/or diffusion information for the time period of the positron emission measurement. Conclusions concerning the perfusion and diffusion in the target tissue can therefore be made. This information can be determined for the whole time period of the measurement, or at least for a part of the measurement time period.

It is thus possible, in addition to the positron emission measurement information, to determine the perfusion and diffusion properties of the tissue to be examined, in order to provide the required supplementation of the results from the positron emission measurement. To do this, the positron emission measurement information from the metabolic processes in the examination area are evaluated taking into account the perfusion and diffusion information obtained with the aid of the second imaging method.

It is thus advantageously possible for examination results from the positron emission tomography to be differentiated in terms of their causes. The signal which is produced by the marker substance can be differentiated in terms of whether the substance was still in the blood stream or was already in the tissue when the signal was recorded.

According to at least one embodiment of the invention, a time frame of the measurement can be generated by way of the images from the second method. If the images obtained with the aid of the second imaging method are generated simultaneously during the entire time period of the positron emission measurement, these images can be used to generate a time frame of the entire examination and, accordingly, a time frame of the perfusion and diffusion processes in the tissue during the measurement time. It is likewise possible to generate such a time frame for only a part of the measurement time period, for example for a time period that is of special significance for the perfusion or diffusion.

With the aid of the time frame, it is possible to differentiate whether the marker substance used in the positron emission measurement, and injected or otherwise administered to the patient, was still in the blood stream or already in the tissue at the time the measurement information was recorded. Particularly in view of the fact that, in the case of a tumor for example, the blood-tissue barrier is especially permeable, this represents important information in assessing the recorded measurement information. Such information in respect of the blood-tissue barrier or its permeability permits conclusions to be drawn on, for example, the age or malignancy of a tumor. The time frame from the second imaging method generally permits a differentiation between early PET signals attributable to perfusion processes and later PET signals resulting from diffusion processes.

According to at least one embodiment of the invention, the perfusion and/or diffusion information can be determined after administration of a contrast agent. The second imaging method then allows conclusions to be drawn regarding the distribution of a contrast agent in the course of time, and this can be included in the evaluation of the positron emission tomography. Some minutes can pass before a marker substance in positron emission tomography and a contrast agent for use with a further imaging method have reached a specific area in the body of the patient to be examined. Positron emission measurement information deriving from signals after a contrast agent bolus has passed through a corresponding section of the blood stream points to diffusion processes. A deficient perfusion, on the other hand, can be established with certainty, by tracking the distribution of the contrast agent in the body area to be examined, and does not lead to incorrect diagnoses.

According to at least one embodiment of the invention, in the context of the evaluation, the positron emission measurement information can be weighted over perfusion and/or diffusion information and/or image information obtained by means of the second method and/or can be allocated to certain processes in the body of the subject being examined. Thus, on the basis of perfusion and diffusion information, measurement information that was obtained in the context of the positron emission measurement can be classified as being more or less informative, for example in respect of a metabolic disturbance that is to be explained. Allocation to certain processes in the body of the subject being examined, for example to a reduced transport of the marker substance in positron emission tomography into the tissue, is made possible, at least with sufficient certainty, only by the additional information. The measurement information processed in this way can be stored together with additional data concerning its weighting and allocation.

At least one embodiment of the invention further proposes that the images can be generated by the second method continuously or at intervals at least during a part of the measurement period. Accordingly, it is possible, over the course of the entire measurement, for images to be generated continuously in parts of the measurement period, whereas in other parts images are generated only at certain intervals. The continuous application of the second imaging method and continuous recording by way of the second imaging method, for the body area to be examined, parallel to the positron emission measurement permits the generation of a very exact time frame and, in the context of the evaluation, takes into account all information that can be determined in the combination of the two methods. Depending on the time resolution provided by the second imaging method, and depending on the questions which are to be elucidated and on which the examination is based, recording images at intervals or continuously only for a part of the measurement period may be sufficient, in order thereby to avoid recording unnecessary data material or to avoid incurring additional costs or to avoid placing an additional burden on the patient.

The evaluated positron emission measurement information can be presented in pictorial form, in particular together with information obtained by way of the second method. The positron emission measurement information, which has been corrected and evaluated taking into account the diffusion and perfusion data from the second imaging method, is advantageously presented in pictorial form in order to give a medical assistant or a physician an overview of the information that has been obtained. Generally, pictorial information is particularly easy for the viewer to take in and remember. The presentation can be provided together with the presentation of information from the second imaging method, for example in order to supplement the information from the positron emission tomography with structural and anatomical information from the second method and to evaluate its information content.

Moreover, the evaluated positron emission measurement information and/or the information obtained by way of the second imaging method can be presented in an image already containing positron emission measurement information. In this case, it suffices to simply add newly arriving measurement information from the positron emission tomography or new information obtained from the second imaging method, as a result of which the time for generating an image can be reduced, if only additional information is input. With rapid determination and evaluation of information, the presentation can then take place almost in real time.

Moreover, a presentation in an image which already contains positron emission measurement information, and which was generated for example at an earlier time of the measurement, that is to say for another time slot, has the advantage that it is possible to monitor developments taking place over time in the recorded signals and information. The same is also possible if the presentation takes place in an image with positron emission measurement information from an earlier measurement or in a reference image attributable to normal functions of the body.

The positron emission measurement information can be presented in different pictorial forms depending on the result of the evaluation, in particular with different color coding and/or in conjunction with further graphic and/or text data. Thus, in view of the question which the examination is intended to answer, a weighting of the obtained measurement information is presented to the medical assistant or physician so that the latter can immediately recognize the different meanings of the individual items of information on the basis of the image presented. Thus, different colors can be used depending on whether, for example, a contrast agent bolus had or had not already passed through a corresponding area at the time the signal was recorded.

For example, in the one eventuality the measurement information can be presented in a red shade, in the other eventuality in a blue shade, and mixed colors can also be used to indicate more differentiated weightings. This can be done, among other things, so that variances or errors in the evaluation or imaging can be taken into account. It is likewise possible for the presented measurement information to be graphically separated according to its weighting, for example by surrounding geometrical elements or by a text which appears when a corresponding image area with associated measurement information is selected with a mouse pointer or the like.

According to at least one embodiment of the invention, the second method used can be a magnetic resonance method and/or computed tomography method and/or ultrasound method and/or a method of optical tomography and/or a magnetic field sensor method and/or a method supplying medical measurement information, in particular perfusion and/or diffusion information, convertible into images. The critical factor for the second method is simply that the time resolution is good enough to permit a differentiation of the measurement information from the positron emission tomography in respect of the perfusion and diffusion properties of the tissue. It is therefore not necessary for the second method to be an imaging method in the traditional sense, and instead it suffices if the measurement information can be converted into images in the sense that a spatial allocation can be effected in order, with the aid of these additional data, to evaluate the positron emission measurement information and if appropriate adapt it.

A method is particularly recommended which, without the danger of damaging the patient, can be used in parallel with and in particular during the whole period of the positron emission measurement, for example magnetic resonance tomography. The choice of the second method is in this case defined by the required time resolution, by the question that is to be explained, and by the severity of a possible disease the patient may have. It is also possible to use, as the second method, a combination of various different methods, for example optical tomography and an ultrasound method. A combination of different medical methods can be effected such that the body area to be examined is covered by these several methods jointly, or also in such a way that each method individually covers the examination area in respect of determining information, in which case supplementary information is obtained, or information items to be corrected by comparison with one another.

The evaluation of the positron emission measurement information can be carried out directly after the end of a part of the measurement period that forms a time slot. Such further processing and subsequent evaluation directly after the completion of a partial measurement allows the evaluated measurement information to be obtained approximately in real time. Accordingly, this evaluated and if appropriate adapted positron emission measurement information can be directly presented in pictorial form, so that it can be assessed, for example by a physician or medical assistant, even during the measurement, taking into account the perfusion and diffusion information from the second imaging method.

Overall, therefore, the informativeness of a positron emission measurement, and the value of such an examination, can thus be greatly increased by the method according to at least one embodiment of the invention, by way of the perfusion and diffusion characteristics being incorporated into the evaluation. It is thus possible in just a single examination step, in a manner convenient for the patient, and with a high degree of accuracy, to establish a diagnosis on the basis of which an optimized treatment of the patient can then be carried out.

BRIEF DESCRIPTION OF THE DRAWINGS

Further advantages, features and details of the invention will become evident from the following illustrative embodiments and from the drawings, in which.

DETAILED DESCRIPTION OF THE EXAMPLE EMBODIMENTS

Figure 1:
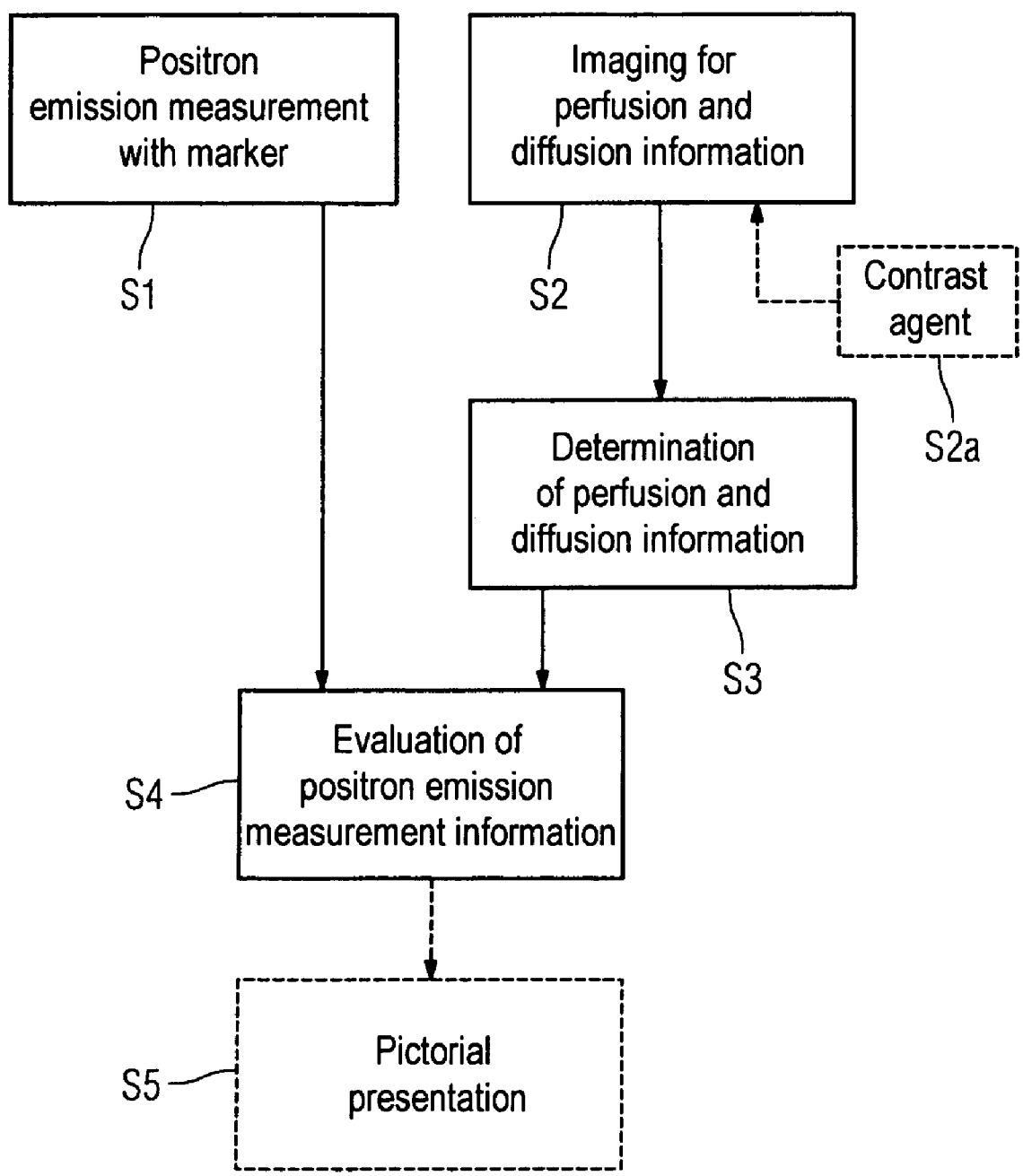
FIG. 1 shows a chart outlining the sequence of a method according to at least one embodiment of the invention.

FIG. 1 shows a chart outlining a method according to the invention comprising steps S1 to S5. In steps S1 and S2, which proceed simultaneously, a positron emission measurement is carried out by means of a marker substance with radionuclides being administered to the subject being examined. The radionuclides emit positrons which interact with an electron, as a result of which gamma radiation is produced in the course of a pair annihilation and is picked up as positron emission measurement information via detectors.

During the time period of the positron emission measurement, images are also continuously recorded in parallel using a second imaging method and, as shown in step S2, these images are used to determine perfusion and diffusion information of the body area to be examined. The determination can, as shown in step S2a, be carried out by administration of a contrast agent, for example in the context of a magnetic resonance examination.

The second imaging method therefore has an improved time resolution compared to the positron emission measurement, so that conclusions regarding the perfusion and diffusion in the target tissue can be reached by, as shown in step S3, determining perfusion and diffusion information.

The information from the two imaging methods is combined and is used, in the context of the evaluation in step S4, for a weighting of the positron emission measurement information, in order thereby to obtain evaluated information which permits differentiation in respect of its origin and its association with certain processes in the body of the subject being examined. This evaluated information can be used, for example, to make a reasoned assessment of the prospects of success of a revascularization procedure.

Although not shown here for sake of clarity, further information from the second imaging method can also be introduced into the evaluation in step S4. Thus, by combining the different imaging methods of positron emission measurement and the second method, a simultaneous measurement of perfusion and metabolism of tumors is possible, for example, in order to monitor the success of certain therapies such as an embolization procedure. Likewise, in neurological and cardiological applications, a differentiation between resting tissue and already dead tissue is possible, for example by combination of positron emission tomography with magnetic resonance tomography.

The evaluation in step S4 can be carried out directly following a time slot of the measurement so that, in a subsequent pictorial presentation, to which reference is made in step S5, the measurement results can be presented almost in real time. The positron emission measurement information, weighted differently as a function of the perfusion and diffusion information, is presented in a color-coded form according to the weighting, so that just by looking at the pictorial presentation it is immediately possible to assess the positron emission information in respect of its informativeness and its association with different physical processes. To obtain a synchronous pictorial presentation in step S5, these additional data are introduced, on conclusion of an evaluation step, into an already existing image with positron emission measurement information.

Figure 2:
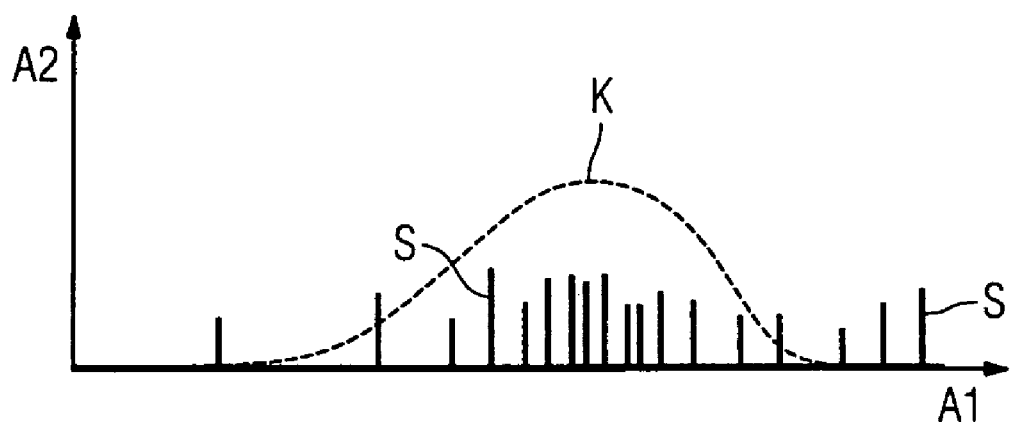
FIG. 2 shows an illustrative graph of recorded measurement information over the course of time, for one location of the area being examined.

FIG. 2 shows an illustrative graph of recorded measurement information over the course of time, for one location of the area being examined. The time is plotted on the horizontal axis A1, while the signal strength is plotted on the vertical axis A2. The individual positron emission signals S, depicted here as bars, are plotted here together with the curve K which represents, only in qualitative terms, the flow of a contrast agent bolus through the corresponding location being examined. The positron emission signals S occur very frequently in the area of the maximum of the curve K, whereas fewer signals S are measured in the area in which the curve K has very low values on the axis A2, particularly in the time period before the arrival of the contrast agent bolus at the location in question. Even after the curve K falls away, signals S still appear, which can accordingly be attributed to diffusion processes that occur later.

A perfusion disturbance in the examined area can thus be established with the aid of the second imaging method, which falls back on the administration of contrast agent, if the transport of the contrast agent and also of the tracer in the positron emission tomography is accordingly inhibited. Thus, the information obtained with the aid of the second imaging method affords the possibility of assigning the positron emission signals S to perfusion or diffusion processes and, as an addition to the conventional ways of assessing positron emission information, affords the possibility of analyzing when and where in the examination area which concentration of the marker substance was available.

Figure 3:
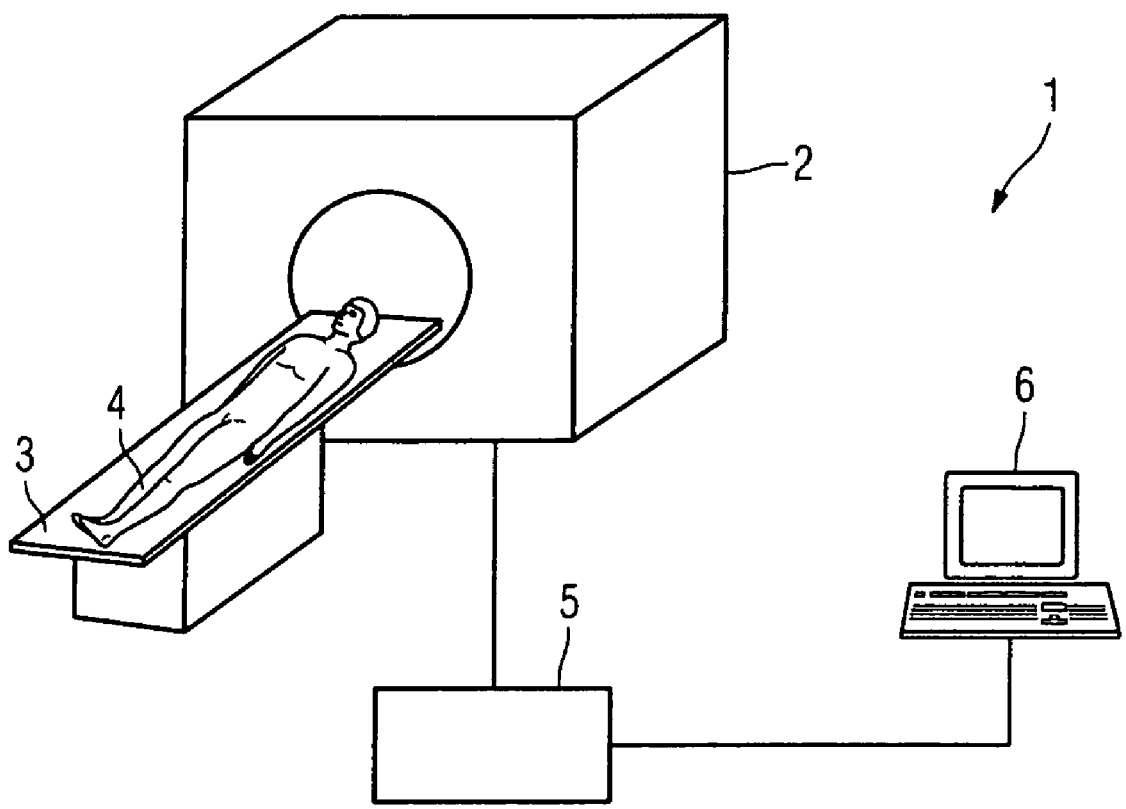
FIG. 3 shows a sketch of an apparatus suitable for carrying out the method according to at least one embodiment of the invention.

FIG. 3 shows a sketch of an apparatus 1 suitable for carrying out a method according to at least one embodiment of the invention. The apparatus 1 comprises a measurement apparatus 2 which permits the recording of positron emission measurement information and of magnetic resonance information. The patient 4 lying on a patient bench 3 is pushed into the measurement apparatus 2 in order for the measurement to be carried out. In the method according to at least one embodiment of the invention carried out here, the positron emission measurement and the generation of images by way of magnetic resonance tomography are carried out simultaneously in the measurement apparatus 2. The measurement information from the positron emission tomography provides indications of functional processes in the body of the patient 4, while the magnetic resonance tomography provides perfusion and diffusion information together with additional structure information.

The information which was recorded in the measurement apparatus 2 is forwarded to a processing apparatus 5 which, from the recorded signals, derives, on the one hand, perfusion and diffusion data and, on the other hand, positron emission data and further image data, the first recorded positron emission measurement information of the measurement apparatus 2 being weighted as a function of the perfusion and diffusion information of the magnetic resonance method carried out in the measurement apparatus 2. The images recorded in the measurement apparatus 2, if these are magnetic resonance images, are used to generate a measurement time frame which is exactly sufficient for resolution of perfusion and diffusion in the body of the patient 4. The evaluated measurement information from the measurement apparatus 2 is then shown pictorially on an image display 6. To do so, the measurement information of the positron emission tomography is introduced, in each case after completion of a time interval of the measurement period, into an already existing image with positron emission information. A synchronous presentation of the measurement carried out in the context of the method according to at least one embodiment of the invention is thus given on the image display 6.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining positron emission measurement information in the context of positron emission tomography, comprising:
    using a marker substance to carry out a positron emission measurement during a measurement time period, in a body area of a subject to be examined, to determine positron emission measurement information;
    scanning the body area to be examined during at least a part of the same measurement time period to obtain data sets with a time resolution suitable for determining at least one of perfusion and diffusion information;
    generating images based on the data sets obtained during the scanning using a second method;
    using the generated images from the second method to determine the at least one of perfusion and diffusion information for at least the part of the measurement time period; and
    evaluating the positron emission measurement information as a function of the at least one of perfusion and diffusion information.

2. The method as claimed in claim 1, wherein a time frame of the measurement is generated by way of the images from the second method.

3. The method as claimed in claim 1, wherein the at least one of perfusion and diffusion information is determined after administration of a contrast agent.

4. The method as claimed in claim 1, wherein, in the context of the evaluation, the positron emission measurement information is at least one of weighted, over at least one of the at least one of perfusion and diffusion information and image information obtained by way of the second method, and is allocated to certain processes in the body of the subject being examined.

5. The method as claimed in claim 1, wherein the scanning is at least one continuous and at intervals during at least the part of the measurement time period.

6. The method as claimed in claim 1, wherein the evaluated positron emission measurement information is presented in pictorial form.

7. The method as claimed in claim 1, wherein at least one of the evaluated positron emission measurement information and the images generated using the second method, are presented in an image already containing positron emission measurement information.

8. The method as claimed in claim 1, wherein the positron emission measurement information is presented in different pictorial forms with at least one of with different color coding, further graphic information, and text data depending on the result of the evaluation.

9. The method as claimed in claim 1, wherein the second method used is at least one of a magnetic resonance method, computed tomography method, ultrasound method, a method of optical tomography, a magnetic field sensor method, and a method supplying medical measurement information related to perfusion and/or diffusion information that is convertible.

10. The method as claimed in claim 1, wherein the evaluation of the positron emission measurement information is carried out directly following the measurement time period.

11. The method as claimed in claim 1, wherein the evaluated positron emission measurement information is presented in pictorial form, together with information obtained by way of the second method.

12. The method as claimed in claim 1, wherein the positron emission measurement information is presented in different pictorial forms depending on the result of the evaluation, with at least one of different color coding and in conjunction with at least one of further graphic and text data.

13. The method as claimed in claim 1, wherein the second method used is at least one of a magnetic resonance method, computed tomography method, ultrasound method, a method of optical tomography, a magnetic field sensor method, and a method supplying medical measurement information, including at least one of perfusion and diffusion information, convertible into images.

14. A computer readable medium storing a computer program, which when executed on a computer, causes the computer to carry out a positron emission measurement during a measurement time period, in a body area of a subject to be examined, to determine positron emission measurement information;

scan the body area to be examined during at least a part of the same measurement time period to obtain data sets with a time resolution suitable for determining at least one of perfusion and diffusion information;

generate images based on the data sets obtained during the scanning using a second method;

use the generated images from the second method to determine the at least one of perfusion and diffusion information for at least the part of the measurement time period; and evaluate the positron emission measurement information as a function of the at least one of perfusion and diffusion information.

* * * * *